United States Patent

Muderlak et al.

[19]

[11] Patent Number: 5,449,117
[45] Date of Patent: Sep. 12, 1995

[54] APPARATUS AND METHOD FOR CONTROLLABLY DISPENSING DROPS OF LIQUID

[75] Inventors: Kenneth J. Muderlak, Shorewood, Wis.; Rocky Shieh, Hsin Chu, Taiwan

[73] Assignee: Technical Concepts, L.P., Elk Grove Village, Ill.

[21] Appl. No.: 129,272

[22] Filed: Oct. 4, 1993

[51] Int. Cl.6 .................................................. A61L 9/14
[52] U.S. Cl. ............................................ 239/6; 222/646;
239/8; 239/35; 239/38; 239/41; 239/70;
239/71; 239/521
[58] Field of Search ................ 239/39, 40, 41, 42,
239/43, 120, 121, 122, 70, 35, 71, 499, 504, 518,
38, 51, 521, 522, 523, 542, 6, 8; 222/645, 646,
647, 648

[56] References Cited

U.S. PATENT DOCUMENTS

| | | | |
|---|---|---|---|
| 752,695 | 2/1904 | Martin | 239/40 |
| 976,992 | 11/1910 | Effantin | 239/43 |
| 1,099,720 | 6/1914 | Peck | 239/40 |
| 1,241,232 | 9/1917 | Macy . | |
| 1,938,219 | 12/1933 | Eckerbom . | |
| 2,075,266 | 3/1937 | Bowman | 239/40 |
| 2,251,734 | 8/1941 | Fuld et al. | 239/41 |
| 2,687,916 | 8/1954 | Reynolds | 239/41 |
| 2,900,139 | 8/1959 | Hensley, Jr. | 239/499 |
| 3,107,860 | 10/1963 | Umbright | 239/521 |
| 3,358,299 | 12/1967 | Maude . | |
| 3,359,063 | 12/1967 | Maude . | |
| 3,668,716 | 6/1972 | O'Hara et al. . | |
| 3,804,592 | 4/1974 | Garbe . | |
| 3,889,881 | 6/1975 | Cunningham et al. . | |
| 4,171,092 | 10/1979 | Ragsdale . | |
| 4,235,373 | 11/1980 | Clark | 239/120 |
| 4,268,285 | 5/1981 | Mason . | |
| 4,294,778 | 10/1981 | DeLuca . | |
| 4,830,791 | 5/1989 | Muderlak et al. . | |
| 4,937,892 | 7/1990 | Syrenne . | |
| 4,984,306 | 1/1991 | Sumerix . | |
| 5,012,961 | 5/1991 | Madsen et al. . | |
| 5,038,972 | 8/1991 | Muderlak et al. . | |
| 5,271,560 | 12/1993 | De Winter | 239/42 |

FOREIGN PATENT DOCUMENTS

| | | | |
|---|---|---|---|
| 2316866 | 2/1977 | France | 239/542 |
| 2618049 | 1/1989 | France | 239/542 |

*Primary Examiner*—Andres Kashnikow
*Attorney, Agent, or Firm*—Welsh & Katz, Ltd.

[57] ABSTRACT

A drop dispensing device includes a liquid ejection system, such as a timed pump mechanism, and a multi-channeled nozzle cooperative with the ejection system, for directing ejected liquid out of a container and into a chamber external to the container wherein the nozzle further includes drip tabs for forming and directing drops. The chamber is divided into a plurality of cavities and is formed by a plurality of interconnected walls. The chamber is adapted to receive the nozzle and includes a raised drainage orifice for each cavity such that the drainage orifice is operatively coupled to a guide tube for simultaneously guiding draining drops from the chamber to a plurality of selected surfaces.

54 Claims, 9 Drawing Sheets

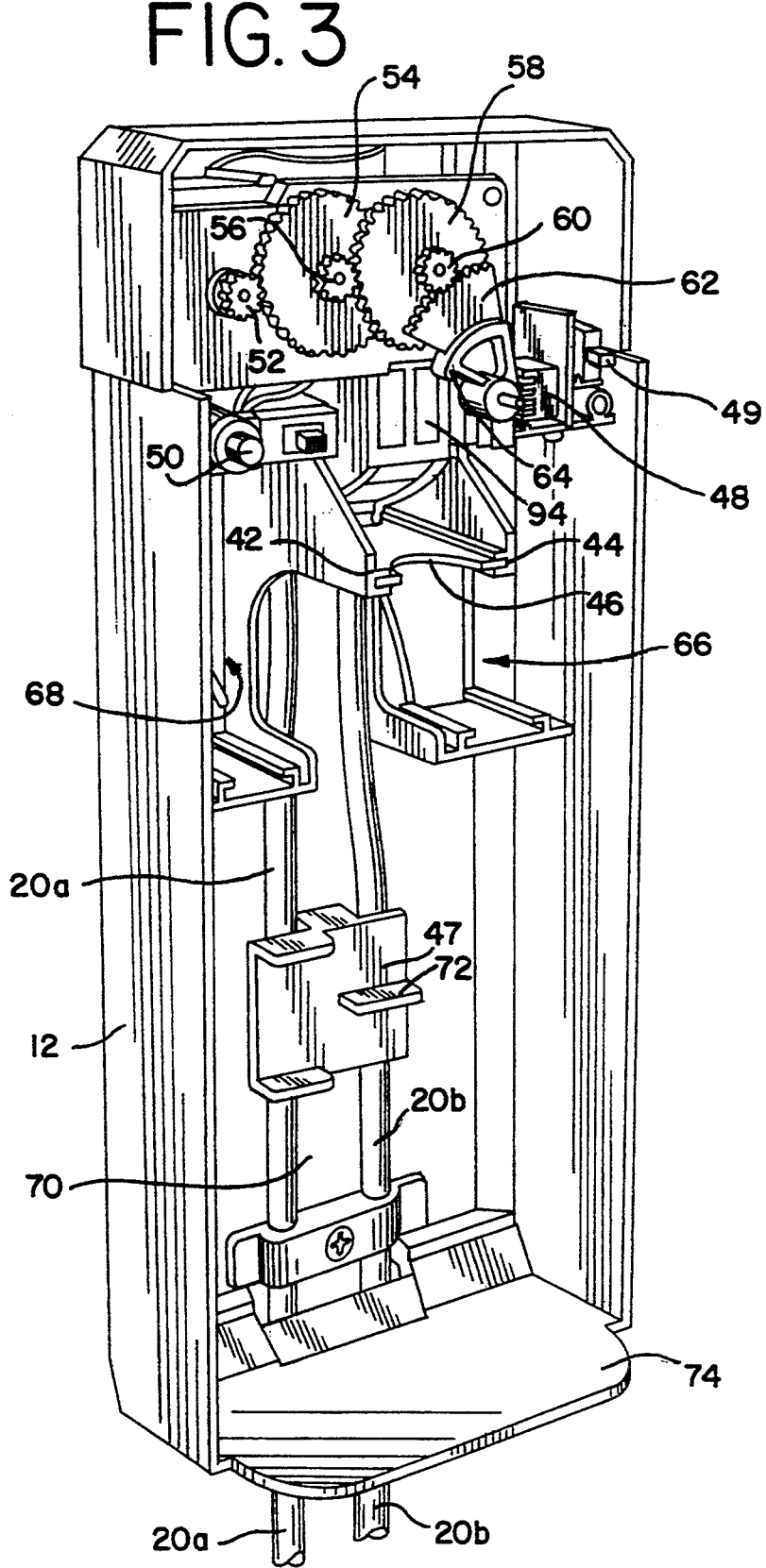

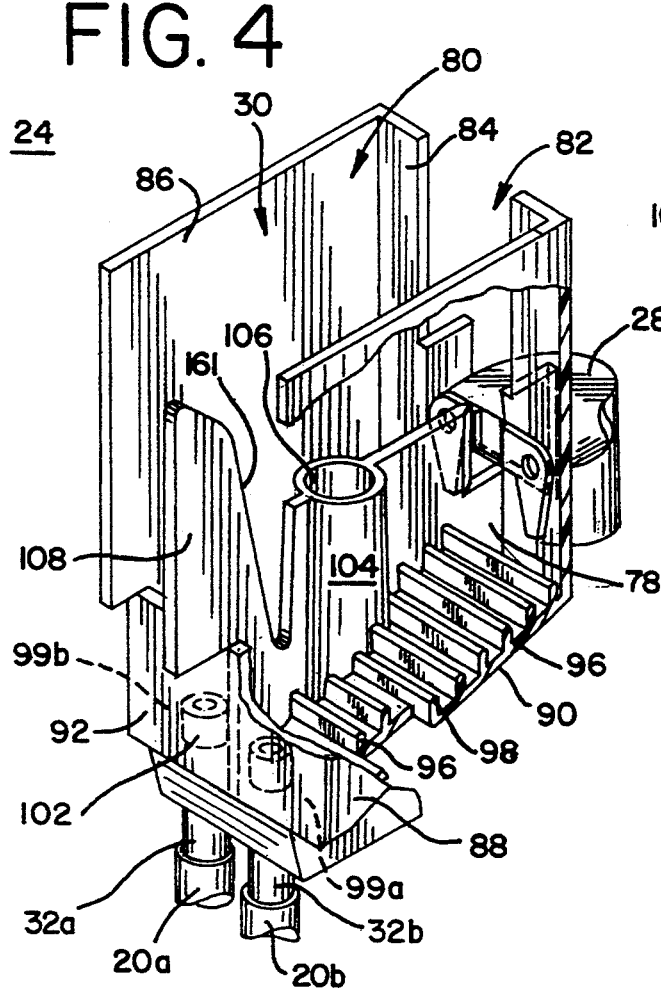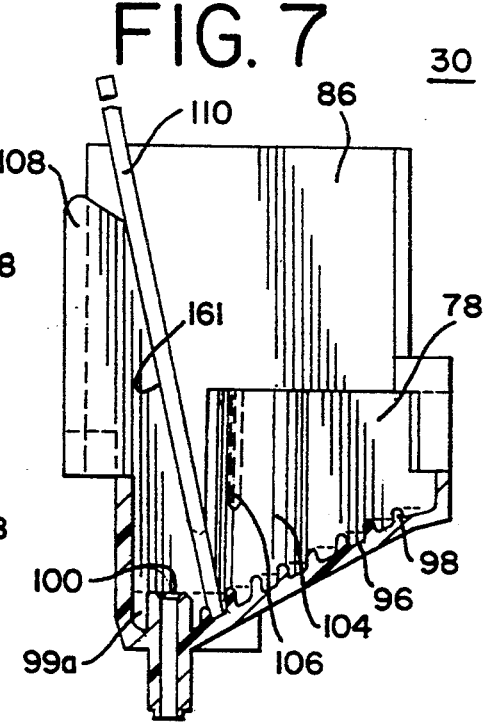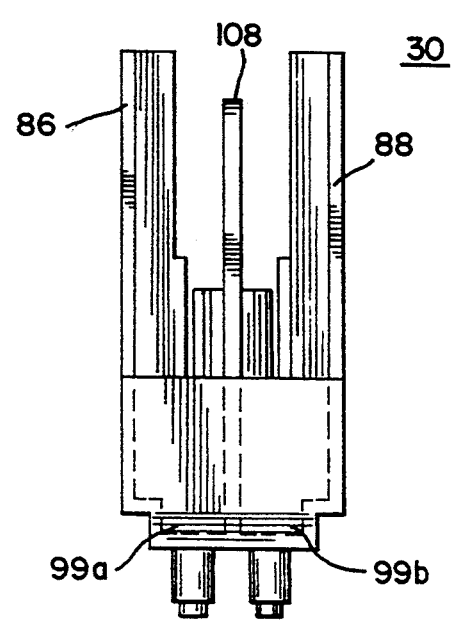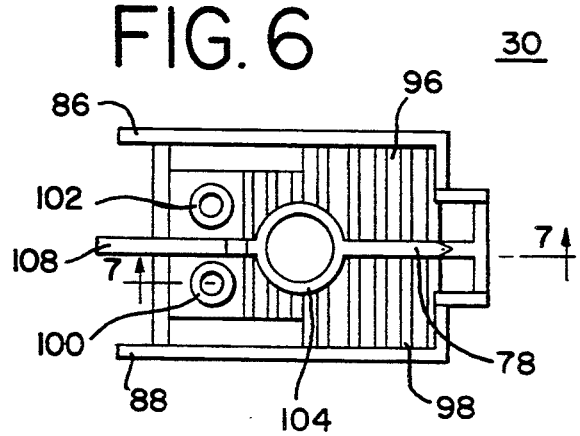

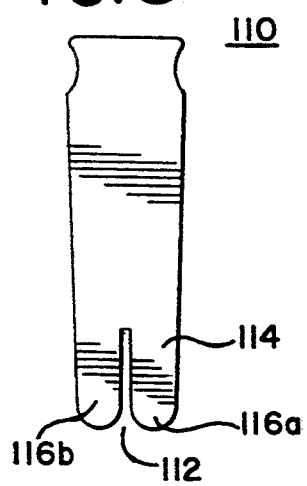
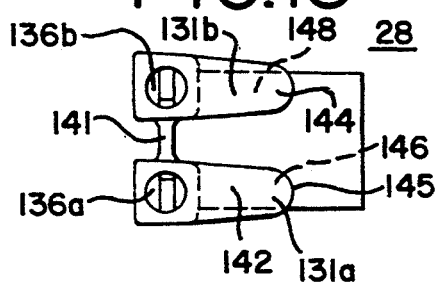
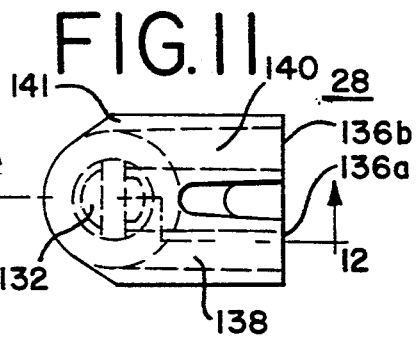
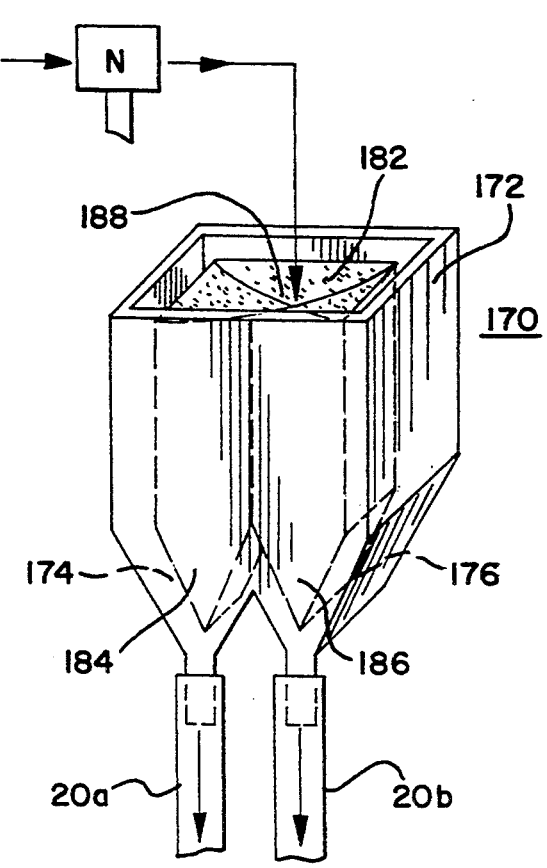
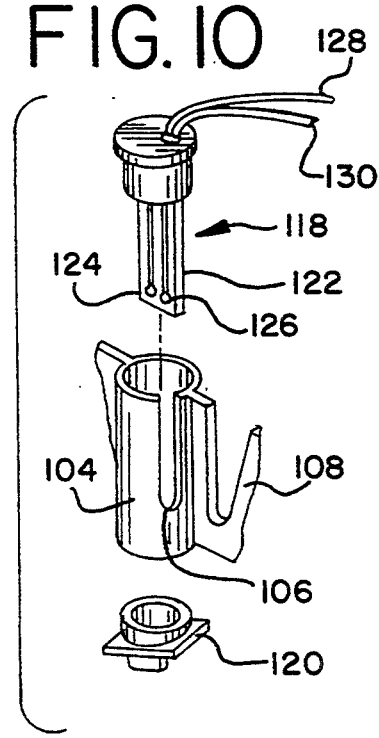
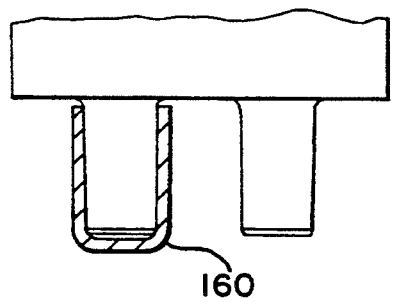

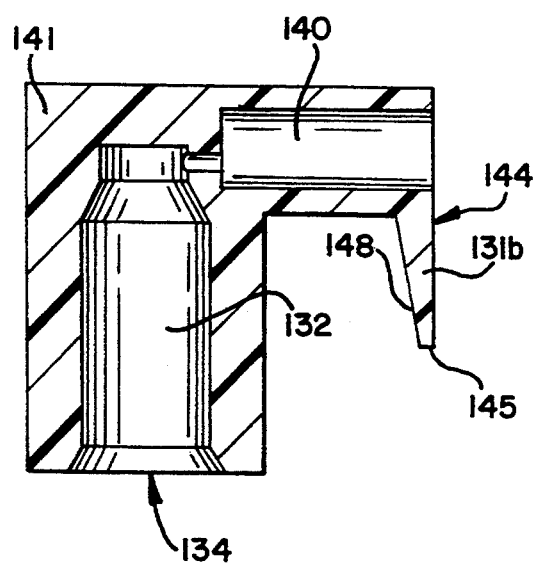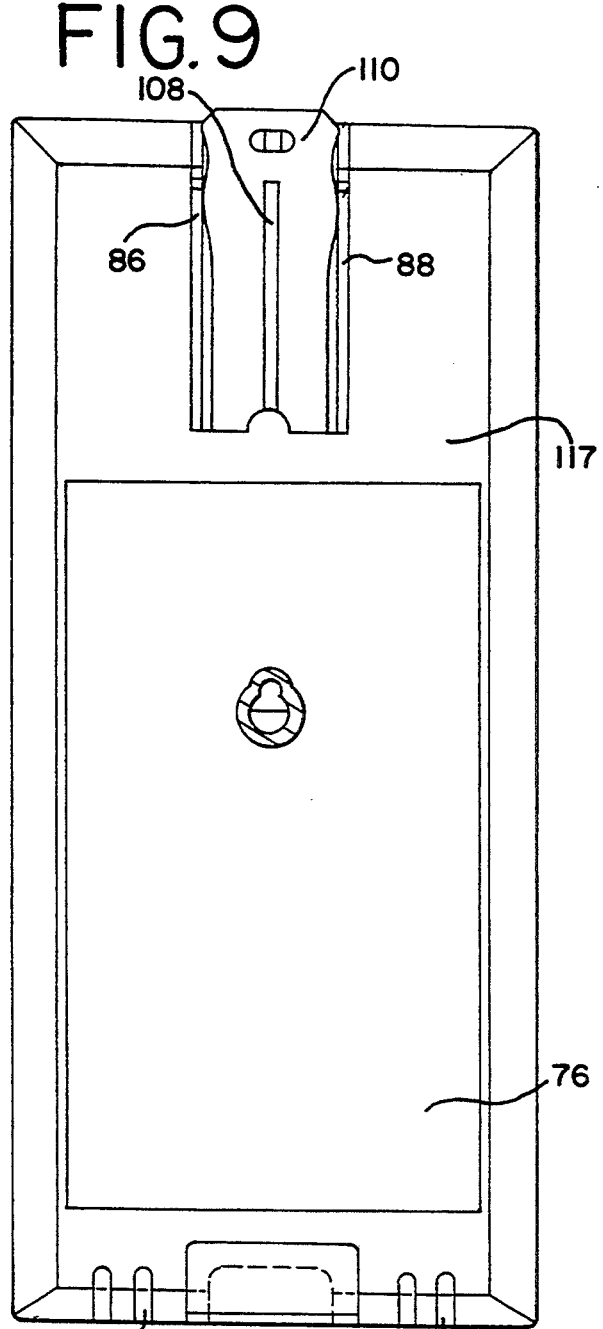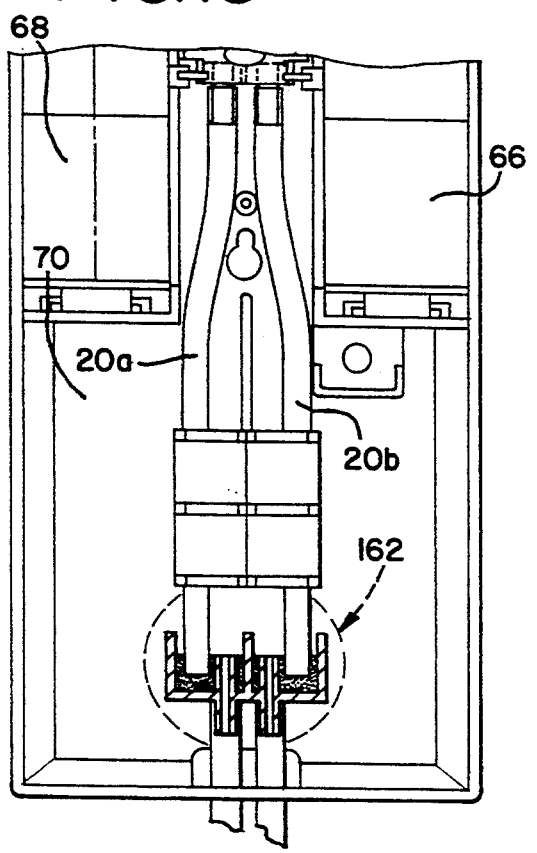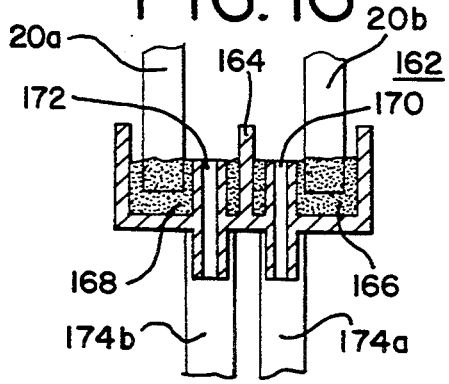

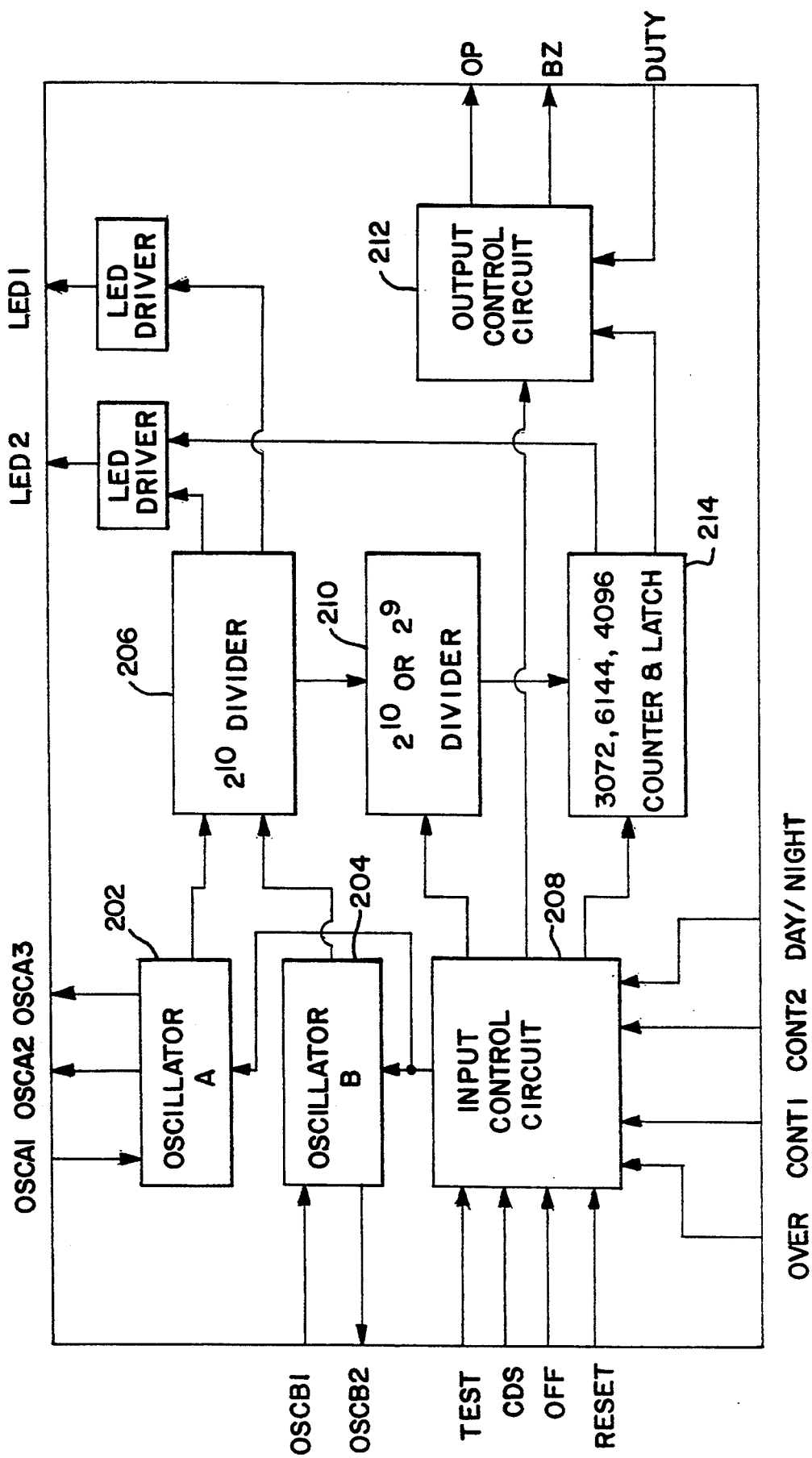

APPARATUS AND METHOD FOR CONTROLLABLY DISPENSING DROPS OF LIQUID

BACKGROUND OF THE INVENTION

The inventive apparatus and method relates generally to devices for controllably dispensing liquids, and more particularly to drip type odorizing and disinfectant liquid dispensers and dispensing methods used by such devices.

Deodorizing and disinfecting treatment systems for urinals and toilet bowls are known which are wall mounted units having wick-type dispensing systems which periodically allow drips of olfactory and biocidal fluid to flow through a tube and onto the surface to be treated, such as the inside of the toilet bowl or inside wall of a urinal. The wicks are generally mounted to absorb fluid from a gravity feed liquid reservoir, while another end of the wick is positioned to drip into a flow tube or other liquid guiding mechanism. At least a portion of the wick is exposed to facilitate odorizing of the surrounding area within a room. Hence, the wick serves as the liquid transfer mechanism between the reservoir and the flow tube and the odorizing medium. With these conventional systems, typically, one deodorizing or disinfecting unit can only treat one urinal.

Several problems exist with conventional wick-type systems since they typically require a number of time consuming and messy steps for installation and servicing. Generally, for installation or servicing, a wick must be inserted in a support tube and subsequently splayed at both of its ends so that the wick properly absorbs the liquid. Furthermore, the wick must typically be adjusted so that a sufficient length reaches either the reservoir of liquid, or the conveying tube to enable the drops to properly flow at a predetermined adjustable rate. The rate is generally adjusted by the size and type of wick used.

There are numerous types of olfactory and disinfectant liquids, and each of these liquids typically have differing viscosities. A wick-type system normally will require a different wick for different viscosities of liquid given that the absorption and flow rates will differ depending upon the viscosity of the liquid. This generally requires the service personnel or user to stock a plurality of different wicks. Where a user decides to use the same wick, the user is often restricted to using liquids having the same viscosity. Also, the wicks transfer (absorb) the liquid molecules with the lowest specific gravity first, such as alcohol or fragrance molecules. Therefore, the fragrance decreases rapidly after only several drops. There exists a need for a liquid dispensing device capable of dispensing a more constant fragrance level throughout the dispensing process.

Another problem occurs with conventional wick-type systems because the reservoir and wicks are typically exposed to the air, thereby allowing dirt and airborne particles to accumulate in the reservoir and on the wick. Consequently, clogging occurs because the wick transfers dirt particles to the flow tube opening.

Other types of deodorizing and disinfecting systems are known which operate based on the flush action of the urinal or toilet and are often in-line devices. One such device is disclosed in U.S. Pat. No. 4,984,306 and is a system for injecting metered amounts of chemicals into flush water as the flush water enters the toilet. A small bore in the injector assembly connects to a chemical reservoir so that the chemical is pulled into the flush water as the flush water passes through the assembly. Such in-line devices are typically costly and require time consuming installation. Also these devices are generally only one-to-one deodorizing units in that only one unit can be installed per each urinal. In addition, such systems are generally not controllable and do not include an air odorizing feature.

SUMMARY OF INVENTION

Accordingly it is a general object of the invention to substantially overcome the above-mentioned problems.

It is a further object of the present invention to provide an apparatus for controllably dispensing drops of liquid which is adapted to deodorize and disinfect a plurality of separate surfaces or areas from one dispensing device.

It is also an object of the present invention to provide a liquid dispensing device capable of dispensing a plurality of liquids having different viscosities without requiring replacement of the drop forming mechanism.

It is also an object of the present invention to provide an apparatus for dispensing liquid which provides simultaneous and multiple fluid flow paths for a single liquid dispensing container such that equal volumes of liquid are dispensed to a plurality of surfaces.

It is a further object of the present invention to provide an apparatus for dispensing liquid which has controlled flow streams through the use of drip tabs on a nozzle to direct the flow of drops from a liquid carrying container to multiple flow streams.

It is an object of the present invention to provide a liquid dispensing device which can direct drops of liquid to selected surfaces to be treated without requiring cumbersome replacement procedures or extensive servicing and installation.

It is yet a further object of the present invention to provide an apparatus for dispensing liquid having a liquid dispensing module adapted with an overflow mechanism to allow selection between multiple flow paths or a single flow path.

It is a further object of the invention to provide an apparatus for dispensing liquid which has an auxiliary reservoir for temporarily storing excessive liquid from being drawn during activation of an in-line flush system.

It is also an object of the present invention to provide an apparatus for dispensing liquid having an overflow detection and shut-off mechanism to prevent liquid from being dispensed when all flow paths are obstructed.

It is yet another object of the present invention to provide an apparatus for dispensing liquid having a wick for dispensing aroma, but not for transferring liquid from a liquid container to a liquid guide mechanism.

It is yet another object of the present invention to provide an apparatus for dispensing liquid wherein liquid is pumped from a container and directed to a diffuser insert which distributes equal amounts of liquid to multiple flow paths to facilitate multiple surface odorizing and/or disinfecting.

It is a further object of the present invention to provide a multiple channel nozzle wherein the multiple channels are designed to have equal back pressure to provide equal volume flow through the multiple channels.

It is another object of the present invention to provide a multiple channel nozzle having drip tabs for forming and directing drops from each of the channels.

The inventive dispensing device dispenses liquid from a container and includes a liquid ejection system, such as a timed pump mechanism, and a mechanism, such as a nozzle, for receiving the ejected liquid and forming the ejected liquid into drops. A chamber external to the container houses the drop forming mechanism. The chamber includes at least one drainage orifice in fluid communication with the chamber to convey drops of liquid out of the chamber.

The nozzle, such as an equal flow multi-channel nozzle, includes drip tabs for forming and directing drops into the chamber. The chamber includes a plurality of cavities formed by a plurality of interconnected walls. The chamber has an aperture for receiving the nozzle and includes a raised drainage orifice in each of a plurality of primary reservoirs at the base of each cavity. Each raised drainage orifice fluidly couples to a flow tube for guiding overflow fluid from the reservoir. As additional liquid is ejected into the chamber, the overflow from the primary reservoir travels down the flow tube and onto a selected surface.

In the preferred embodiment, the chamber has a first of the interconnected walls lying inclined below the drip tabs of the nozzle and has a plurality of adjacent fluid wells for temporarily trapping ejected liquid to facilitate evaporation for odorizing. When the fluid wells are full, each additional drop from the nozzle tabs flows to the primary reservoir. Each primary reservoir is in fluid communication with the raised drainage orifice at the base of the chamber and temporarily houses the ejected liquid as it moves down the inclined fluid wells. A wick, having an end in each of the primary reservoirs, absorbs fluid from the primary reservoirs. Another end of the wick extends out an opening in the device to provide aroma to the surrounding area.

Control circuitry selectively activates a pump mechanism to periodically dispense drops out of the nozzle. The pump actuation rate is selectable. The control circuitry allows the selection between single or multiple flow tubes so that the dispensing device may be used to dispense drips down one flow tube or multiple flow tubes. A selectable flow circuit allows a user to vary the amount of liquid that is dispensed over a predetermined period of time so that light or heavy amounts of liquid may be dispensed.

The control circuit also includes a selectable light sensing circuit to facilitate automatic dispensing of a predetermined amount of drops when the device detects that sufficient light is available after a long period of darkness, such as when the dispenser detects that morning has arrived. The control circuitry further includes a selectable automatic mode and a twenty-four hour operating mode so that the dispensing device only operates when there is a predetermined amount of light or operates continuously through darkness such as during evening hours. A selectable multi-tone indication circuit generates an audible response when the device determines that the liquid container must be replaced. In addition, the controlled circuitry includes a pulse width modulated battery indication signal for a light emitting element, such as a light emitting diode, that varies the pulse width when the control circuit determines that the liquid container must be refilled. The control circuitry further includes an automatic motor shut off circuit for inhibiting the motor when a predetermined number of pulses occurs.

In another embodiment, the dispensing device includes an overflow detection system that detects excessive levels of liquid in the primary reservoir. An overflow sensor generates an overflow indication signal that causes the device to cease pumping. The selectable multi-tone audible circuit indicates that an overflow is occurring in the overflow stack. The control circuitry produces an audible indication, distinct from the refill audible signal, indicating that an overflow condition exists.

In another embodiment, the dispensing device includes a secondary reservoir that collects liquid from the primary reservoir. During in-line connections, such as for in-line urinal connection, the secondary reservoir serves as the source of disinfecting liquid. Evaporated aroma from the secondary reservoir is sucked out through a vacuum effect caused during flushing to prevent aroma from the chamber from being removed during flushing.

In another embodiment, a diffuser insert, such as a piece of absorbent material, replaces the divided chamber and fluid wells. Instead, drops from the nozzle are absorbed by the diffuser and diffused to multiple flow tubes in equal amounts. The diffuser includes pointed protruding fingers that extend from a bottom of the diffuser into respective flow channels.

In another embodiment, the fluid wells are removed and the fluid travels directly down the inclined wall into the primary reservoir.

A method for dispensing liquid in drop form is disclosed which includes ejecting the liquid through the nozzle from the container at predetermined intervals using a timed actuator mechanism; forming drops of liquid by directing the ejected liquid over a drip tab extending about an exit orifice of the nozzle into the chamber; and conveying resulting drops from the chamber.

BRIEF DESCRIPTION OF THE DRAWINGS

FIG. 3 depicts a perspective view of the dispensing device in accordance with the invention having the front cover removed and a front portion of the support structure cut away to show the interior of the dispensing device without a container or batteries.

FIG. 4 illustrates a perspective view of a drop forming assembly having a chamber and nozzle in accordance with the invention.

FIG. 5 is a rear view of the chamber of FIG. 4.

FIG. 6 is a plan view of the chamber shown in FIG.

FIG. 7 is a cross-section of FIG. 6 taken along lines 7—7.

FIG. 8 depicts a front view of a wick in accordance with the invention.

FIG. 9 is a rear view of the dispensing device with a portion of an odorizing wick extending out an opening therein.

FIG. 10 is an exploded perspective view of an overflow detection arrangement in accordance with the invention.

FIG. 11 depicts a top view of a nozzle with drip tabs in accordance with the invention.

FIG. 12 depicts a cross-sectional side view of the nozzle of FIG. 11 taken along line 12—12.

FIG. 13 depicts a front view of the dual channel nozzle of FIG. 11 showing the drip tabs in accordance with the invention.

FIG. 14 shows a plug inserted over a drainage extension for converting the device from a dual tube mode to a single tube mode.

FIG. 15 is a partial view of the back portion of the support structure of the device having a secondary reservoir.

FIG. 16 depicts the secondary reservoir of FIG. 15.

FIG. 17 is a block diagram of an integrated circuit for use as part of the control circuitry in accordance with the invention.

FIG. 19 is a perspective view of another embodiment of a drop dispensing device having a diffuser insert.

DETAILED DESCRIPTION OF THE PREFERRED EMBODIMENTS

Although the below description will be made with reference to liquids for odorizing and disinfecting urinals, it will be understood that the inventive dispensing device may be used for controllably dispensing any suitable chemical such as chlorine for pools or other liquids.

Figure 1:
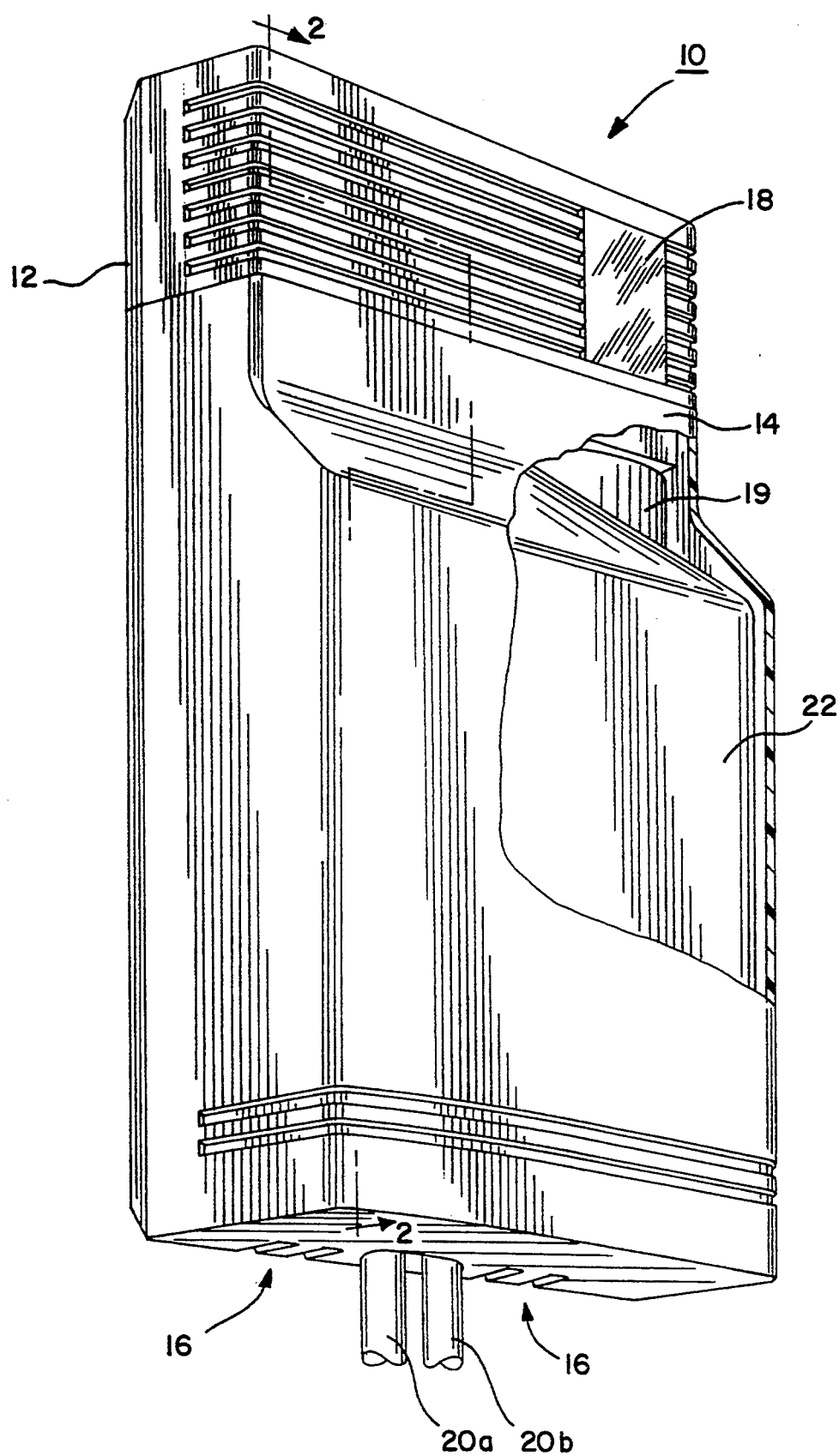
FIG. 1 shows a perspective view of the dispensing device in accordance with the invention having a portion of the front cover cut away to illustrate the interior of the dispensing device.

FIG. 1 is a perspective view of the drip dispensing device 10 in accordance with the invention. The dispensing device 10 includes a support structure 12 and a hinged cover 14, part of which is shown cut away exposing the interior of the dispensing device 10. The support structure 12 includes vents 16 for allowing air flow through the device and a view window 18 for facilitating visual status of various aspects of the dispensing device 10 as will be described later. A portion of one of a plurality of 1.5 VDC "D" size batteries 19 is exposed. A pair of conveying tubes 20a and 20b exit the support structure 12 through the bottom and will also be discussed in detail later. An outer surface of a liquid container 22 is also shown.

Figure 2:
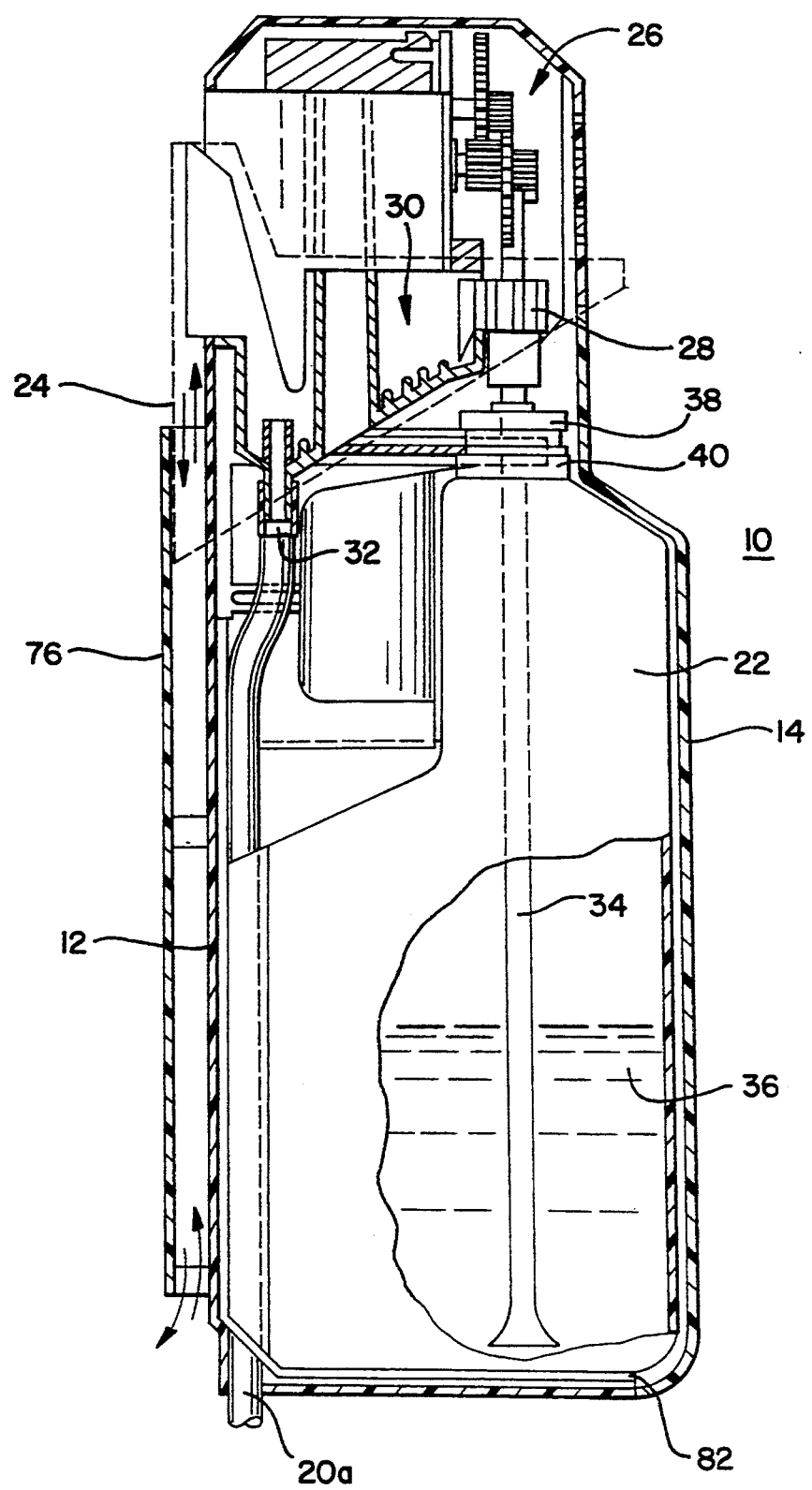
FIG. 2 depicts a cross-sectional view taken along line 2—2 of FIG. 1 and illustrates one of the embodiments of the dispensing device in accordance with the invention.

Referring to FIGS. 2 and 3, the support structure 12 houses drop forming assembly 24 and a controlled liquid ejection system generally indicated at 26. The drop forming assembly 24 includes a multi-channel nozzle 28, a drop forming chamber 30, and the conveying tubes 20a and 20b coupled to the chamber 30 via respective tube sleeves generally indicated at 32. The conveying tubes direct liquid from the chamber to a selected surface, such as a urinal surface.

The container 22 includes hollow pump stem 34 which directs the olfactory and/or disinfecting liquid 36 from one end and couples to the nozzle 28 at its other end. The container 22 has a ferrule 38 located above a collar 40. The support structure 12 has a pair of integrally formed mounting grooves 42 and 44 for receiving a metal holding bracket 46 which holds the collar 40 in place. The container 22 includes a plurality of specifically oriented indentations (not shown) molded into the bottle which serve as a keying mechanism. The support structure 12 includes corresponding keys in the form of protrusions 72 which mate with the indentations on the container so that only properly keyed containers may be inserted into the support structure.

Liquid container 22 has a groove to allow the passage of the liquid flow tubes 20a and 20b around the container. Since the flow tubes 20a and 20b are positioned down the center of the support structure 12 along the back surface, the groove allows the passage of the flow tubes through the bottom of the support structure.

A switch array 48, such as a dual in-line package switch, allows a user to selectively modify the operation of the device as will be described. An on/off switch 49 and a reset switch 50 are also accessible when the hinged cover 14 is opened.

The liquid ejection system 26 (FIG. 3) includes a speed reduction transmission system. The transmission system includes a main pinion gear 52 driven by a drive motor. The pinion gear 52 couples to a drive gear 54 having a pinion gear 56 which in turn couples to an intermediate gear 58. The intermediate gear 58 has an actuator drive gear 60 which engages an actuating member 62, such as a segment gear or the like. The actuating member 62 has a cam 64 for contacting the top of the nozzle 28 to depress the nozzle. A spring under the nozzle or in the container causes the nozzle to rise after being depressed. However, it will be recognized that any suitable pump actuating mechanism may be employed.

The support structure 12 includes a pair of integrally formed holding cavities 66 and 68 for housing a pair of 1.5 volt D-cell batteries which supply power to a control circuit. A back wall 70 supports a tube clamp 47 for securing the flow tubes 20a and 20b in place. As shown, the key protrusions 72 are integral with the tube clamp 47. A bottom support shelf 74 serves to support the container 22 after it is inserted into the support structure 12. A convection plate 76 (FIG. 2) piggybacks to the back wall 70, via a pair of bosses or other attachment mechanism, to form an air flow passage shown by arrows along the back of the device as will be described later.

FIG. 4 is a partial cut away perspective elevational view of the drop forming assembly 24 wherein the chamber 30 is partitioned via center partition wall 78 into two cavities 80 and 82. Each cavity is formed by a plurality of interconnected walls. The walls may be separate walls or they may be shared walls as shown. The walls forming the chamber 30 include a back wall 84 slotted to receive nozzle 28, opposing side walls 86 and 88, downwardly sloping bottom wall 90, and front wall 92 which is located opposite back wall 84. Each cavity 80 and 82 includes an open top area through which vapor from liquid stored in each cavity may escape.

The chamber 30 may be integrally formed as a module that may snap fit into the support structure 12. Also, the cavities 80 and 82 may be integrally formed as part of the support structure 12. The cavities 80 and 82 have an opening 94 (see FIG. 3) for receiving the dispensing end of nozzle 28. The opening 94 is such that the nozzle 28 is prevented from contacting the downwardly sloping wall 90 when the nozzle is completely depressed by the actuator.

Referring to FIGS. 4, 5, 6 and 7, a portion of the downwardly sloping wall 90 includes a plurality of adjacent fluid wells 96. The fluid wells 96 are formed by a plurality of protruding ribs 98 which extend outwardly from downwardly sloping bottom wall 90 and form fluid wells to temporarily trap olfactory/disinfecting liquid ejected from the nozzle 28. The fluid wells provide greater fluid surface area to facilitate evaporation of the aroma molecules from the liquid to deodorize surrounding air. The liquid is trapped in the fluid wells 96 until additional drops are delivered by the nozzle 28.

Each cavity 80 and 82 includes a primary reservoir 99a and 99b. A portion of the downwardly sloping bottom wall 90 and side and rear walls of the chamber define the two primary reservoirs 99a and 99b. The primary reservoirs 99a and 99b are located at the base of the chamber 30. When all of the fluid wells and primary reservoirs are full of liquid, a raised drainage orifice 100 and 102 in each primary reservoir receives drops of liquid from the reservoirs as the nozzle delivers another drop of liquid. Under the force of gravity, drops flow down the flow tubes 20a and 20b. Distal ends of flow tubes 20a and 20b are positioned proximate the selected surface in the urinal so that drops traveling through the flow tubes contact the desired surface.

The center wall 78 includes an integrally formed overflow stack 104 with overflow slot 106. The center wall 78 includes an oblique slotted rib portion 108 which serves as a support rib for a wick 110 (FIG. 7). As best seen in FIG. 5, the slotted rib portion 108 is slightly thicker than the side walls 86 and 88 to provide additional structural support for the wick 110.

Referring to FIGS. 7 and 8, the wick includes a slot 112 at its base end 114. The base end 114 includes two extensions 116a and 116b. The slot 112 slidably engages with the oblique slotted rib 108 so that the wick 110 lies in a slanted position toward the back of the dispensing device. The wick 110 rests transversely with respect to the slotted rib 108. Each of the fingers 116a and 116b rests in each of the primary reservoirs 99a and 99b to absorb the olfactory and/or disinfecting liquid to provide a constant odorizing effect. The wick 110 may be made of any suitable absorbent material such as cloth or other suitable material.

As shown in FIG. 9, the wick 110 extends out of the rear opening in the back 117 of the support structure to allow aroma from the wick to disperse into the surrounding air. Air current flowing through the air passage formed by the convection plate 76 passes over the wick 110 to odorize the surrounding air.

Referring to FIG. 10, the integrally formed stack 104 serves as a housing for a flow level detector sensor 118. A plug 120 may be inserted in the bottom of the hollow stack 104 to prevent liquid from flowing out of the stack. In operation, if all flow tubes clog, the liquid will begin to rise and eventually drain into the stack through overflow slot 106. This overflow will cause the stack to be filled with liquid whereafter the flow level detector 118 will detect an unsuitable liquid level and send a signal to control circuitry to inhibit further dispensing of liquid. The flow sensor 118 may be a simple circuit board 122 with a pair of electrical leads 124 and 126 connected to respective lead wires 128 and 130. When the liquid is at a predetermined level, the liquid will short the two lead ends 124 and 126 together forming a short circuit, thereby indicating an overflow condition.

FIGS. 11-13 depict one embodiment of the multi-channel nozzle 28 fabricated from plastic and having a pair of drip tabs 131a and 131b, an inner cavity 132 with a receiving orifice 134 adapted to receive the stem in the container, and exit bores 136a and 136b at the end of a pair of fluid channels 138 and 140 defined by a nozzle body 141. The fluid channels 138 and 140 are generally cylindrically shaped with the same cross-sectional area. Since each channel has the same dimensions and shape, fluid passing through the channels exits with the same pressure. The bores 136a and 136b are of the same size and shape. The dual fluid channels 138 and 140 are also of substantially equal size and shape so that ejected liquid flows in an equal amount out of each of the fluid channels. The fluid channels 138 and 140 merge into the common inner cavity 132. The fluid channels 138 and 140 are spatially disposed to allow liquid to be directed into separate cavities inside chamber 30. The displacement between the fluid channels may be any suitable amount depending upon the configuration of separate cavities in the chamber 30 (FIG. 6).

The drip tabs 131a and 131b are proximate the exit orifices 136a and 136b. The drip tabs 131a and 131b serve both to help form drops and to direct ejected liquid into chamber 30. The drip tabs 131a and 131b are integrally formed at the exit orifices 136a and 136b, respectively, of each of the fluid channels 138 and 140.

Each of the drip tabs include a first downwardly extending surface 142 and 144 respectively, for receiving the fluid to form drops of the fluid as the fluid flows over the first surface. Each of the first surfaces 142 and 144 has a tip 145 at the bottom end thereof, and each tab further includes a second surface 146 and 148 respectively, opposite the first surface. The second surface extends away from the tip 145 at an angle equal to or less than ninety degrees with respect to the first surface to prevent the flow of fluid along the second surface. As shown, the tip includes an intermediate surface between the first and second surface. However, it will be recognized that the tip may come to a point so that the first and second surfaces are directly joined. Each of the first surfaces 142, 144 tapers inwardly towards the tip 145 of the tab to direct the flow of fluid drops to the tip of the tab as the fluid drops are formed on each first surface.

The drops are formed as a function of the surface tension along the length of the tab and the rate at which the liquid is forced through the nozzle. It is most desirable to control the pump action to insure that liquid is not ejected too rapidly or under too much pressure so that the ejected liquid flows over the drip tabs.

In an alternative embodiment, the drip tabs may be removed from the nozzle and the liquid may be ejected onto a drop forming surface separate from the nozzle. For example, a drop forming surface on the wick or other surface may be used to form the droplets whereafter the drops drain into the primary reservoirs.

Referring to FIG. 14, the dispensing device having two or more flow tubes may be converted to a single flow tube dispensing system by using a plug 160 and selecting single tube operation as will be described later. The plug 160 is insertable over the tube sleeve extension 32 which defines the drainage orifice from chamber 30. Referring to FIGS. 4 and 13, when the system is configured as a single dispensing device, the oblique slot 161 (FIG. 4) in the center rib 108 serves as a fluid by-pass channel to allow fluid from one primary reservoir to flow to an adjacent primary reservoir. The overflow slot 106 is higher than the oblique slot 161 so that fluid will flow to an adjacent reservoir before entering the overflow stack.

Referring to the embodiment of the invention disclosed in FIGS. 15 and 16, a secondary reservoir 162 serves to prevent unsuitable disturbance of the primary reservoirs 99a,b when the dispensing system is connected as an in-line fluid dispensing system. As previously mentioned, when an odorizing or disinfecting system is connected as an in-line system, such as for urinals or the like, the flush process typically causes a vacuum effect through the flow tubes whereafter the vacuum draws the air borne fragrance out of the chamber. This is undesirable when an odorizing feature is desired.

The secondary reservoirs 162 are in serial fluid communication with the primary reservoirs 99a,b and are located between the primary reservoirs 99a and 99b and the outlet of the ends of the flow tubes 20a,b. A center wall portion 164 separates a first secondary reservoir 166 from a second secondary reservoir 168. Each of these secondary reservoirs operate substantially the same as the primary reservoirs 99a or 99b. Hence, when the fluid reaches a level above raised orifices 170 or 172, the fluid flows down through the orifices and into the flow tubes 174a and 174b, respectively. When flushing occurs, the aromatic or air-borne molecules proximate the secondary reservoir are drawn into the main flush line of the urinal so that the primary reservoirs 99a,b are substantially unaffected. Hence, fragrance in the chamber 30 is not removed when the urinal or toilet is flushed.

Figure 18:
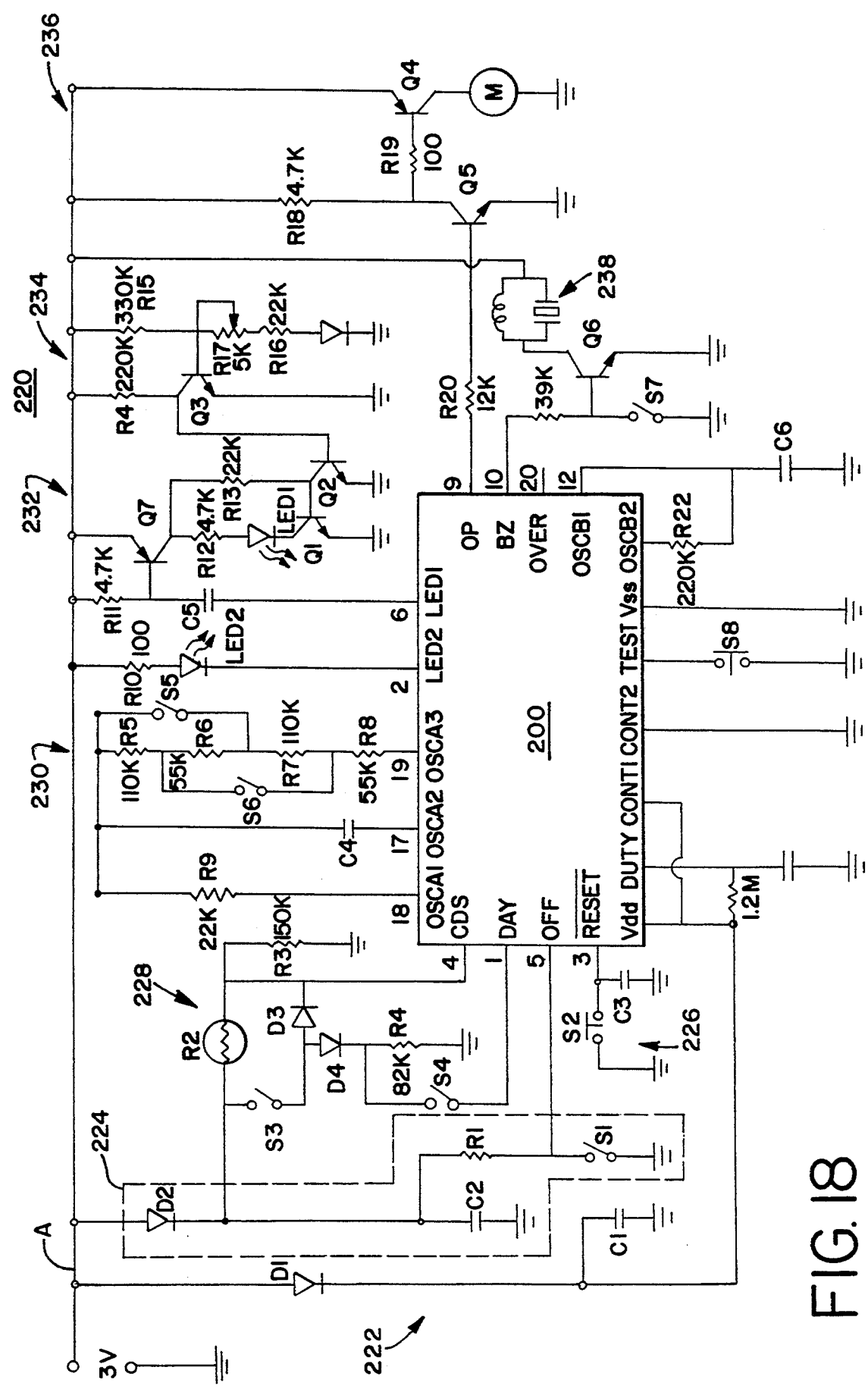
FIG. 18 is a circuit diagram of an embodiment of the control circuitry for the drop dispensing device in accordance with the invention.

Referring to FIGS. 17 and 18, a block diagram generally depicts an integrated circuit (IC) 200 for use as part of a control circuit 220 for operating the dispensing device. The IC 200 is preferably a model TC-2020 manufactured by Holtek Microelectronics Inc., Taiwan. However, any suitably programmed microcomputer or other discrete circuitry may also be used. The IC 200 includes an oscillator circuit A 202 for providing oscillator outputs OSCA2 and OSCA3 and for receiving a variable oscillator input OSCA1. The IC 200 further includes another oscillator circuit B 204 which provides an oscillator output OSCB2 and receives an oscillator input signal OSCB1. The oscillator A 202 and oscillator B 204 provide pulses (an input frequency) to a divider circuit 206. The number of pulses (the input frequency) varies in accordance with resistance changes that are selectable by a user through a selectable switching arrangement to be described later.

An input control circuit 208 receives various inputs as shown and generates an output signal to the oscillator circuits 202 and 204 and to another divider 210 to vary the oscillator outputs based on input signals received by the input control circuit 208. The input control circuit 208 also provides signals to an output control circuit 212 and a counter and latch circuit 214. The output control circuit 212 provides output pulse OP to activate the drive motor to periodically depress the nozzle. For example, during normal operation, a pulse interval of a predetermined number of counts that corresponds to approximately 15 minutes is set so that an output pulse OP occurs every 15 minutes to eject liquid.

The output control circuit 212 also includes a multi-tone audible signal generating circuit that generates an output buzzer pulse BZ (buzzer) to activate an external buzzer circuit. The output control circuit 212 receives a DUTY signal set up by an R/C combination (R and C in FIG. 18) that determines the duty cycle of the OP signal. The R/C combination is chosen so that the motor has enough time to depress the nozzle. The output circuit 212 also receives a counter/latch signal from the counter/latch circuit 214 that indicates when a predetermined time out period has occurred, such as when a total of 3,072 or 6144 pulses have been output (e.g., the container is empty) so that the motor may be inhibited after the time out period occurs. The counter and latch circuit 214 also indicates to the output control circuit when the pulse interval has elapsed.

The divider 206 divides the input frequency from the oscillator circuits into a visual flash pulse signal to LED driver circuits (FIG. 17) to activate or deactivate LED's based on whether a set number of counts have been counted by the divider. The LED2 driver supplies a 1/16 duty cycle pulse to LED2 (FIG. 18). This duty cycle pulse is latched by counter and latch 214 at a maximum counter time corresponding to when a refill is required, such as when the count 6144 corresponding to a bottle empty condition occurs.

The LED1 driver helps drive a power indicator LED1 (FIG. 18) that is flashed "on" when sufficient battery power exists to actuate the nozzle and is "off" when the battery should be changed.

FIG. 18 depicts the IC 200 with support circuitry to complete the control circuit 220 for operation of the dispensing device. The control circuit 220 includes a memory backup circuit 222 formed by diode D1 and capacitor C1 to provide a suitable voltage level to the IC 200 when power is removed. A power supply circuit 224 includes the "on/off" switch S1 (switch 49 in FIG. 3) coupled to a current limiting resistor R1, such as a 220 K ohm resistor. The circuit limiting resistor couples to a filtering capacitor C2 and diode D2. A reset circuit 226 formed by the "reset" momentary switch S2 (switch 50 in FIG. 3) and a capacitor C3 allows the integrated circuit 200 to be manually reset upon the depression of the "reset" switch S2. For example, when a container is emptied a new container is inserted into the device whereafter the user resets the control circuitry to again begin the timing and control process.

A light sensing circuit 228 includes a photo-sensitive element, such as a photo resistor R2 which has a resistance which varies with the amount of light sensed by the resistor R2. An "auto/24 hr." switch S3 serves as the selection switch to choose between continuous operation (24 hour operation) or automatic operation (operation when enough light is present in the room). When the "auto/24 hr." switch is closed, the power line A connects to the CDS pin through diodes D2 and D3 thereby bypassing the photo resistor R2 indicating to the input control circuit that a continuous twenty four hour operation has been selected. Resistors R3 and R4 serve as current limiting resistors. A voltage level on the CDS pin indicates how much light is detected. The output pin OP is controlled in response to the amount of light detected.

A "day/night" switch S4 allows a user to select between a day and night mode. The switch S4 in combination with the "auto/24 hr." switch S3 provide a selectable morning mode or evening mode. To select the morning mode (e.g., day), the "auto/24 hr." switch S3 is open, indicating the automatic mode. A counter in the input control circuit, such as a divide by fifteen counter, is used to calculate a preset time period during which an insufficient amount of light is sensed, e.g., the amount of time set to indicate that a night condition exists. When the "day/night" switch S4 is open, producing a high voltage level in the DAY pin, and the CDS pin is set to a low voltage (not enough light), the counter starts to count. If there is insufficient light for a night threshold period of approximately 15 times the pulse interval of fifteen minutes, the control circuit assumes a nighttime condition. After the CDS pin later goes high, indicating that morning has arrived, (e.g., enough light for a long enough period of time), the output control circuit outputs four pulses (OP) to the drive motor in a short period of time (approximately four seconds) to quickly eject four pulses of liquid into the chamber 30. This feature is designed to increase the fragrance level in the morning after no liquid was dispensed during the night. If a darkness period is less than the night threshold period, the control circuit assumes that light is being sensed periodically and the counter is reset each time the CDS pin indicates that sufficient light has been sensed.

Below is a time chart used to illustrate how to calculate and define the night threshold period for the different frequency settings based on the setting of various switches:

a. 225 minutes (15 time outs ×15 minute interval) when the device is in single/lite mode;

b. 112.5 minutes (15 time outs ×7.5 minute intervals) when the device is in single/heavy mode;

c. 112.5 minutes (15 time outs ×7.5 minute intervals) when the device is in the two/lite mode; and d. 56.23 minutes (15 time outs ×3.75 minute intervals) when the device is in the two/heavy mode.

Conversely, the control circuit may also output quick pulses when the control circuit determines that nighttime has arrived. When the "day/night" switch S4 is closed and the "auto/24 hr." switch S3 is open, the IC 200 generates four quick output pulses (OP) at the beginning of the time when too little light has been sensed for a predetermined period of time to indicate that nighttime has arrived.

During the 24 hour mode, the switch S3 is closed and the output control circuit generates an output pulse OP every fifteen minutes during morning and night conditions without generating the quick pulses during the morning and night transitions.

A variable frequency selection circuit 230 allows a user to select between a single tube mode or a dual tube mode and allows a user to select the amount of liquid to be dispensed between a light and heavy amount. The variable frequency selection circuit 230 includes a "one/two" switch S5 to select between one flow tube or two flow tubes. When the switch S5 closes, resistors R5 and R6 are shorted out so that the series combination of R7 and R8 in conjunction with capacitor C4 and resistor R9 to set the oscillator A to generate oscillator output pulses at a first frequency, indicating that two tubes have been selected.

When the switch S5 is open, resistors R5 and R6 are not shorted out and are in series with resistors R7 and R8. Therefore the input to the oscillator A changes so that the output from the oscillator A changes to a second frequency.

A "light/heavy" switch S6 when closed shorts resistors R6 and R7 thereby leaving the series combination of R5 and R8 in conjunction with C4 and R9 to provide the same frequency as that when switch S5 is closed and S6 is opened, if resistors R5 and R7 are of the same value as shown in FIG. 18, thereby indicating that a heavy amount of fluid is required. When both switches S5 and S6 are closed indicating two flow tubes are selected and the heavy dose of fluid is required, resistor R5, R6, and R7 are in parallel. Thus, the total resistance of resistor R8 in series with the R5-R6-R7 parallel combination is less than when either switch S5 or S6 is open, and the effect, in combination with resistor R9 and capacitor C4, is to generate another frequency indicating that more fluid must be output.

The CONT1 pin is tied high and the CONT2 pin is tied to ground so that a maximum count of output pulses (ejections from the nozzle) is 6144 before the control circuit determines that the container is empty. Different combinations of high or low voltage levels on these pins can vary the maximum count of output pulses on OP.

A battery saving circuit 232 varies the duty cycle of a battery indicator pulse to the LED1 from ½ to 1/120th of the full duty cycle after a predetermined count of divider 206. Hence the battery saving circuit serves as a pulse width modulating circuit for a light emitting element that varies the pulse width of a control signal to the light emitting element after a predetermined amount of liquid has been dispensed. The battery saving circuit includes resistors R11, R12, PNP transistor Q7 and input capacitor C5. Input capacitor C5 and R11 form an input pulse to Q7 which varies the control signal for LED1 from a ½ "on" duty cycle to a 1/120th "on" duty cycle. The transistor Q7 acts as an amplifier and wave form shaper and R11 is a current limiting resistor.

A battery low voltage detect circuit 234 determines when the battery drops below a predetermined threshold set by a voltage divider including R15, R16 and variable resistor R17. The variable resistor may be adjusted to vary the low battery threshold level. The battery low voltage detect circuit and LED1 drive circuit include Q1, Q2, Q3 and associated components. In operation, when the battery voltage falls below the threshold voltage, Q3 turns off, Q2 turns on, Q1 turns off and LED1 shuts off.

The visual indicator LED2 is activated when the number of OP pulses reaches the predetermined maximum pulse count to indicate that the container is empty and must be changed. The counter and latch 214 supplies a maximum pulse count signal to energize LED2.

A motor driver circuit 236 through transistors Q5 and Q4 and resistors R19 and R20 provide sufficient drive current for motor M which activates the cam to depress the nozzle.

An oscillating buzzer circuit 238 generates an audible tone when output BZ goes high, which occurs when the counter counts to the maximum pulse count of 6144 OP pulses, thereby audibly indicating that the container is empty. Another distinct tone is generated when the flow level detector pin OVER indicates an improper amount of fluid in the overflow stack in response to receiving an overflow detection signal from the fluid level sensor 118.

A "tone/quiet" switch S7 when closed serves to short a base of transistor Q6 to ground thereby shutting off the transistor Q6 and preventing an audible tone from occurring. Hence, switch S7 allows a user to select between a quiet mode or the audible tone mode. Resistor R22 and capacitor C6 serve to set the frequency for the oscillator B. An optional switch S8 on the test line of the IC, when depressed, forces the integrated circuit into a self-test mode.

The optical emitting devices LED1 and LED2 and the optical detector R2 communicate with the ambient air through view window 18 located in the upper portion of the support structure 12 as shown in FIG. 1.

Each of the switches S3, S4, S5, S6 and S7 may be one switch in a multiple switch dual in-line package (DIP).

Referring to FIG. 19, an alternative drop forming assembly 170 is shown. The assembly 170 includes a housing 172 having a plurality of drainage areas 174 and 176 and a liquid absorbent diffuser 182 such as cloth, sponge or other suitable liquid-absorbent material, formed having protruding fingers 184 and 186 located at a bottom of the diffuser 182. The diffuser 182 receives drops from a nozzle, such as nozzle 28, which is actuated by the actuating mechanism 26 to dispense drops onto a top center surface 188 diffuser 182. Through each of the protruding fingers 184 and 186, the diffuser 182 evenly distributes equal amounts of liquid into the dual flow guide tubes 20a and 20b. As with the preferred embodiment shown in FIGS. 2, 3 and 18, the ejection mechanism includes an electronically actuated motor; a cam moved by the motor; and a nozzle depressed by the cam to eject liquid from the container. Any suitable nozzle may be used since the diffuser performs the function of absorbing the liquid and evenly dispensing the liquid into a plurality of flow tubes.

Figure 20:
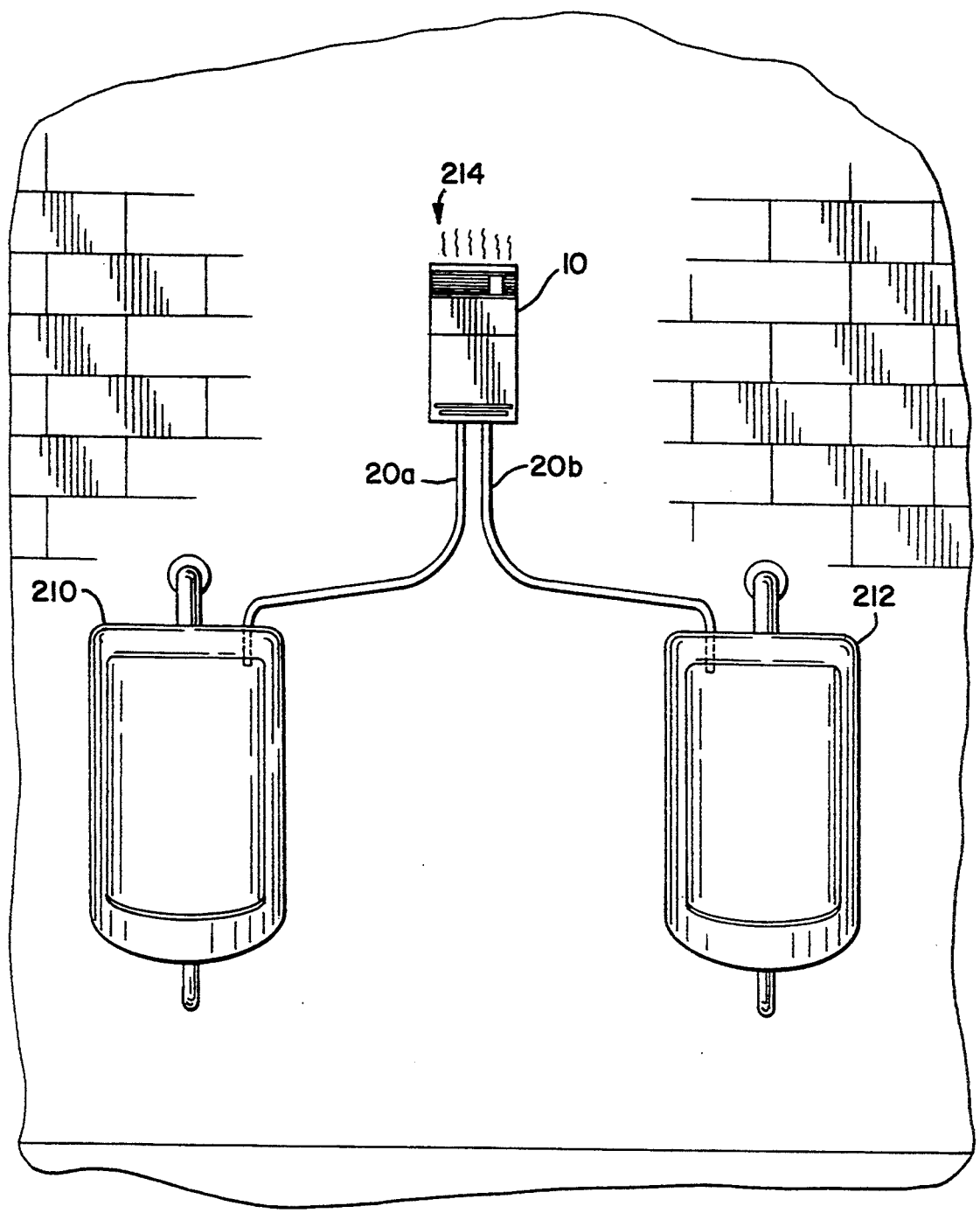
FIG. 20 is a perspective view illustrating placement of the dispensing device on a wall to facilitate disinfectant for multiple urinals and odorizing of a single room.

FIG. 20 pictorially illustrates the dispensing device 10 mounted to a wall for simultaneously disinfecting two urinals. Guiding tubes 20a and 20b each go to a separate urinal 210 and 212, respectively. These guiding tubes 20a and 20b may be affixed to the wall or to the urinals 210 and 212 in any suitable manner. Lines 214 indicate the vapor being expelled from the cavity inside the device when the pump means is actuated thereby providing fragrance to the air surrounding the dispensing device 10.

In operation, the control circuit, set for a specific depression frequency, activates drive motor M which causes the cam 64 to depress the nozzle 28. The olfactory liquid 36 is ejected by the subsequent pump action into the cavities 80 and 82 through nozzle 28. Preferably, the amount of depression force and the rate at which the nozzle is depressed is adjusted so that the liquid does not spray onto the wick and instead travels down the drip tabs 131a and 131b. However, where ejected liquid sprays onto the wick 110, the wick will serve to drain the liquid into the primary reservoirs 99a,b since the wick is already saturated. This may occur due to the change in viscosity of the liquid being dispensed. For example, a liquid with a high viscosity may not spray into the chamber in the same manner as a lower viscosity liquid.

The drip tabs 131a and 131b are positioned to direct drops onto the inside surface of the downwardly sloping wall 90. As drops are dispensed, they continue to flow over the ribbed surfaces 98 and into the fluid wells 96 from one adjacent fluid well to another toward the raised drainage orifice 100. When the fluid wells and primary reservoirs 99a,b are filled, each additional drop from the tabs 131a,b causes an amount of liquid in the primary reservoir equal to a drop to flow out of the raised orifices 100, 102 and down the conveying tubes 20a,b. Thereafter, the drops continue to travel down the guiding tubes 20a and 20b at a rate predetermined in part by the rate at which drops fall from the tabs. Accordingly the dispensing device simultaneously dispenses equal amounts of fluid down two conveying tubes.

The "on/off" switch 49 (switch S1 in FIG. 18) affects the application of voltage to the control circuitry. The liquid ejection system is controlled so that the nozzle 28 will be periodically depressed to dispense approximately 28 ounces of liquid in a 60-day period. The pump (e.g., nozzle and stem) may be a 110 milliliter pump or any suitable pump. A predetermined count is determined which corresponds to the number of depressions necessary to dispense the entire amount of liquid during that 60-day period. Once the predetermined count is reached, the refill LED2 is activated.

The "one/two" switch S5 allows the user to choose between a single tube system or a double tube system. This is typically done only once at the time of installation. Switching from a single tube to a double tube system causes the pump depression frequency to be doubled to allow for the same volume per hour to flow into the dual drip tubes 20a and 20b instead of a single tube. Consequently, the volume of liquid dispensed reduces the refill time to 30 days. With a dual tube system, the depression frequency is approximately one depression every five minutes as opposed to a ten minute depression frequency for a single drip tube system.

The "light/heavy" switch S6 allows the user to vary the depression frequency according to desired fragrance levels. For example, when the one/two switch S5 indicates a dual tube configuration, the depression frequency is usually one depression every five minutes but may be adjusted by the fragrance level switch to a depression frequency of one depression every five minutes (light mode) or to one depression every 3.75 minutes (heavy mode) depending on the desired odorizing level.

A method for dispensing liquid in drop form from a container using the above described device includes ejecting the liquid through the nozzle at predetermined intervals using a timed actuator circuit; forming drops of liquid by directing the ejected liquid over a drip tab extending from an exit orifice of the nozzle; and conveying the drops from the chamber through a fluid path that is in fluid communication with the chamber.

Since the nozzle may have two equally sized channels, the method may include the step of ejecting substantially equal volumes of liquid out of a plurality of channels in the nozzle during each predetermined interval. The convection plate and wick combination facilitates the emitting of vapor produced from the drops in the chamber to odorize an area in a room.

Another method for dispensing liquid in drop form from a container using one embodiment of the dispensing device includes ejecting the liquid through the nozzle at predetermined intervals using a timed actuator circuit; directing the ejected liquid over a series of fluid wells in a chamber that receives the nozzle; and guiding the drops from the chamber to a selected surface through a guide tube connected to the chamber.

In an alternative embodiment, the depression frequency may be adjustable between a set range using variable resistance potentiometers, or any suitable mechanism for adjusting the depression frequency timer to time out at different intervals. Any suitable timing circuit may be used. As with any chosen depression frequency, the counter continues to count the number of depressions and indicates a refill condition after the count reaches the predetermined count.

When the "auto/24 hr." switch S3 is set in the "auto" position, the light sensing circuit 228 will turn the dispensing device off when there is insufficient illumination in the room. This allows the conservation of olfactory liquid and battery power during periods in which the urinal or toilet bowl is not being used.

LED1 is a low battery level LED indicator and is visible through the view window 18 to provide the user with an indication of a low battery level so that replacement can be effectuated prior to complete power loss by the 3-volt power source. An AC/DC adapter may also be incorporated into the device so that the dispensing device 10 may be plugged into an AC wall socket.

Servicing of the inventive device to replace an empty container 22 is effectuated by a single-step process. The user removes or opens cover 14 and slides the container 22 and attached nozzle 28 out of support structure 12 and merely inserts a full container (with nozzle) in its place by sliding the full container forward so that the nozzle properly interacts with the dual cavities 80 and 82 through openings 94.

Consequently, there is no need to physically contact any wet wicks or otherwise adjust the drip mechanism to facilitate proper servicing of the device. The nozzle 28 is designed to emit an equal flow of liquid each time the pump is depressed so that a metered amount of olfactory liquid is always ejected, whereas with conventional wick systems, the length of the wick or incomplete spraying will affect flow rate and amount of dispensed liquid.

The dual cavities 80 and 82 allow a single container 22 to supply predetermined amounts of olfactory liquid to a plurality of different urinals. One will recognize that more than two cavities may be incorporated into the device so that a corresponding number of urinals may be odorized/disinfected using a single dispensing device.

The air passage defined by the back wall 70 and convection plate 76 allows air to flow over the portion of the wick that extends out of the back of the chamber to dispense olfactory vapors to the surrounding area. Flow of air through the air passage in an upward or downward direction also draws vapor from inside the chamber out of the open back portion of the chamber. It will be recognized that any suitable air flow generating feature may also be employed, such as a motorized fan or other mechanism.

The preferred embodiment illustrates the use of a dual cavity system or a chamber divided by a partition wall with corresponding dual tubes to supply drops to a plurality of selected surfaces, however, it will be recognized that a single chamber or single cavity may also be employed with a corresponding single fluid conveying tube to allow the inventive dispensing device to be adapted for a single flow tube.

It will be recognized that the type of liquid used may affect the rate at which vapor is generated since varying chemicals may have different chemical compositions that allow olfactory molecules to evaporate while having disinfecting molecules remain in liquid form so that drops of the disinfectant have a greater probability of reaching the area to be disinfected. In addition, it may be useful to use the aforementioned system for controllably dispensing non-olfactory liquids so that the wick and air flow passage need not be used.

Specific embodiments of a novel apparatus and method for controllably dispensing drops of liquid have been described for the purpose of illustrating the manner in which the invention may be used and made. It should be understood that the implementation of other variations and modifications of the invention in its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. A liquid dispensing device for controllably dispensing drops of liquid from a container comprising:
    power actuated means operating upon an actuator associated with the container for selectively ejecting liquid from the container;
    means associated with the actuator for receiving the ejected liquid and forming the ejected liquid into drops;
    a chamber, external to the container, in which the liquid drops are formed by the receiving and drop-forming means;
    the chamber having at least one drainage orifice in fluid communication with the chamber to convey drops of liquid out of the chamber.

2. A liquid dispensing device for controllably dispensing drops of liquid from a container comprising:
    means for ejecting the liquid from the container;
    means for receiving the ejected liquid and forming the ejected liquid into drops;
    a chamber, external to the container, in which the liquid drops are formed by the receiving and drop-forming means;
    the chamber having at least one drainage orifice in fluid communication with the chamber to convey drops of liquid out of the chamber;
    the chamber including a primary reservoir for collecting drops of liquid dispensed from the receiving and drop-forming means and wherein the drainage orifice is in the primary reservoir and is raised above a floor of the primary reservoir to receive liquid when the primary reservoir accumulates a predetermined level of liquid.

3. The liquid dispensing device of claim 2 wherein the means for receiving the ejected liquid and forming the ejected liquid into drops includes a nozzle in fluid communication with the container.

4. A liquid dispensing device for controllably dispensing drops of liquid from a container comprising:
    means for ejecting the liquid from the container;
    means for receiving the ejected liquid and forming the ejected liquid into drops;
    a chamber, external to the container, in which the liquid drops are formed by the receiving and drop-forming means;
    the chamber having at least one drainage orifice in fluid communication with the chamber to convey drops of liquid out of the chamber;
    control means for controlling the ejecting means to periodically dispense the liquid from the container.

5. The liquid dispensing device of claim 4 wherein the control means comprises:
    a selectable flow circuit for varying the amount of liquid that is dispensed from the container over a predetermined period of time.

6. The liquid dispensing device of claim 4 wherein the control means comprises:
    a selectable light sensing circuit having a photosensitive element for detecting light energy and for generating a signal when the photo-sensing element detects light after a predetermined period of darkness.

7. The liquid dispensing device of claim 4 wherein the control means comprises:
    a selectable multi-tone indication circuit that generates a first audible output in response to determining that a predetermined amount of liquid has been dispensed.

8. The liquid dispensing device of claim 7 further comprising:
a timer generating periodic pulses at predetermined intervals;
a counter means accepting said periodic pulses, said counter means generating a latch signal Upon receipt of a predetermined number of periodic pulses, wherein said first audible output is activated as a result of said latch signal for notifying the user of said liquid dispensing device of the need for replacement of the container.

9. The liquid dispensing device of claim 7 wherein the selectable multitone indication circuit further comprises:
means for generating a second audible output in response to determining that a liquid overflow condition has occurred.

10. The liquid dispensing device of claim 4 wherein the control means comprises:
a pulse width modulating circuit for a light emitting element that varies the pulse width of a control signal to the light emitting element after a predetermined amount of liquid has been dispensed.

11. The liquid dispensing device of claim 4 wherein the control means comprises:
motor shut off circuit means for inhibiting a liquid dispensing motor when a predetermined amount of liquid has been dispensed.

12. The liquid dispensing device of claim 11 further comprising:
a timer generating periodic pulses at predetermined intervals;
a counter means accepting said periodic pulses, said counter means generating a latch signal upon receipt of a predetermined number of periodic pulses, wherein operation of said motor is inhibited as a result of said latch signal.

13. The liquid dispensing device of claim 4 wherein the control means comprises:
liquid overflow detection means for detecting a level of liquid in a primary reservoir which receives the liquid, and for generating a level indication signal to inhibit the ejecting means.

14. The liquid dispensing device of claim 13 wherein the control means further comprises:
audible tone generating means for producing an audible output in response to the level indication signal.

15. The liquid dispensing device of claim 13 wherein the detection means further comprises a slotted overflow stack and a fluid level sensor in communication with the fluid in the stack for generating an overflow indication signal wherein the slot in the overflow stack receives overflow liquid from the primary reservoir and the fluid level sensor generates the overflow indication signal when the fluid level in the overflow stack reaches a predetermined level.

16. The liquid dispensing device of claim 13 wherein the liquid overflow detection means further comprises:
an overflow stack which receives overflow liquid from the primary reservoir; and
a fluid level sensor in communication with the liquid in the stack for generating the level indication signal when the fluid level in the overflow stack reaches a predetermined level.

17. The liquid dispensing device of claim 4 wherein the control means further comprises:
means for adjusting a time period that determines when to periodically dispense the liquid; and
means for selecting between a single flow path volume and a multiple flow path volume to vary the time period in response to selecting either the single flow path or the multiple flow path.

18. The liquid dispensing device of claim 4 wherein the chamber includes a primary reservoir for accumulating drops of liquid dispensed from the receiving and drop-forming means, and the device further comprises means, in fluid contact with the primary reservoir, for absorbing a portion of the liquid to facilitate aromatic dispensing of a portion of the liquid in the primary reservoir.

19. The liquid dispensing device of claim 4 wherein the control means comprises:
an empty-indicator circuit that generates a visual signal in response to determining that a predetermined amount of liquid has been dispensed.

20. The liquid dispensing device of claim 19 further comprising:
a timer generating periodic pulses at predetermined intervals;
a counter means accepting said periodic pulses, said counter means generating a latch signal upon receipt of a predetermined number of periodic pulses, wherein said visual signal is activated as a result of said latch signal for notifying the user of said liquid dispensing device of the need for replacement of the container.

21. The liquid dispensing device of claim 4 wherein the control means comprises:
a battery low voltage detect circuit that generates a visual signal to show whether a power source for the control means has dropped below a predetermined threshold voltage.

22. The liquid dispensing device of claim 4 wherein the control means includes:
a timer generating periodic pulses at predetermined intervals;
a counter means accepting said periodic pulses, said counter means generating a latch signal upon receipt of a predetermined number of periodic pulses.

23. A liquid dispensing device for controllably dispensing drops of liquid from a container comprising:
means for ejecting the liquid from the container;
a nozzle in fluid communication with the container for receiving the ejected liquid and forming the ejected liquid into drops;
a chamber, external to the container, in which the liquid drops are formed by the nozzle;
the chamber having at least one drainage orifice fluid communication with the chamber to convey drops of liquid out of the chamber;
the nozzle comprises an internal fluid channel, having a receiving orifice for receiving liquid from the container and an exit orifice, and a downwardly positioned drip tab coupled to the exit orifice.

24. A liquid dispensing device for controllably dispensing drops of liquid from a container comprising:
means for ejecting the liquid from the container;
means for receiving the ejected liquid and forming the ejected liquid into drops;
a chamber, external to the container, in which the liquid drops are formed by the receiving and drop-forming means;

the chamber having at least one drainage orifice in fluid communication with the chamber to convey drops of liquid out of the chamber;

means for mating with the container to allow only corresponding keyed containers to be inserted into the device.

25. A liquid dispensing device for controllably dispensing drops of liquid from a container comprising:

means for ejecting the liquid from the container;

means for receiving the ejected liquid and forming the ejected liquid into dropsy;

a chamber, external to the container, in which the liquid drops are formed by the receiving and drop-forming means;

the chamber having at least one drainage orifice in fluid communication with the chamber to convey drops of liquid out of the chamber;

the chamber is formed by a plurality of interconnected walls wherein at least a first of the interconnected walls slopes downwardly toward the drainage orifice and includes a plurality of fluid wells for temporarily storing ejected liquid.

26. The liquid dispensing device of claim 25 wherein the plurality of fluid wells is formed by a plurality of adjacent protruding surfaces extending outwardly from the first wall such that ejected liquid is temporarily trapped in the fluid wells as the liquid travels toward the drainage orifice.

27. A liquid dispensing device for controllably dispensing drops of liquid from a container comprising:

means for ejecting the liquid from the container;

a nozzle in fluid communication with the container for receiving the ejected liquid and forming the ejected liquid into drops;

a chamber, external to the container, in which the liquid drops are formed by the nozzle;

the chamber having at least one drainage orifice in fluid communication with the chamber to convey drops of liquid out of the chamber;

the chamber including a primary reservoir for accumulating drops of liquid dispensed from the nozzle;

means, in fluid contact with the primary reservoir, for absorbing a portion of the liquid to facilitate aromatic dispensing of a portion of the liquid in the primary reservoir;

a tab extending from an exit of the nozzle, said tab having a first downwardly extending surface for receiving the liquid to form drops of the liquid as the liquid flows over the first surface.

28. The liquid dispensing device of claim 27 wherein the first surface has a tip at the bottom end thereof, the tab further comprising a second surface opposite the first surface, the second surface extending away from the tip of the first surface at an angle less than ninety degrees with respect to the first surface to prevent the flow of liquid along the second surface.

29. The liquid dispensing device of claim 27 wherein the first surface tapers inwardly towards a tip of the tab to direct the flow of liquid drops to the tip of the tab as the liquid drops are formed on the first surface.

30. A liquid dispensing device for controllably dispensing drops of liquid from a container comprising:

means for ejecting the liquid from the container;

means for receiving the ejected liquid and forming the ejected liquid into drops;

a chamber, external to the container, in which the liquid drops are formed by the receiving and drop-forming means;

the chamber having at least one drainage orifice in fluid communication with the chamber to convey drops of liquid out of the chamber;

the chamber including a primary reservoir for accumulating drops of liquid dispensed from the receiving and drop-forming means;

a secondary reservoir that receives fluid from the primary reservoir through serial fluid communication for facilitating evaporation of liquid and having a drainage orifice for receiving fluid overflow from the secondary reservoir; and a liquid flow guide connected to the drainage orifice for guiding liquid from the secondary reservoir.

31. A liquid dispensing device for controllably dispensing drops of liquid from a container comprising:

means for ejecting the liquid from the container;

a nozzle in fluid communication with the container for receiving the ejected liquid and forming the ejected liquid into drops;

a chamber, external to the container, in which the liquid drops are formed by the nozzle;

the chamber having at least one drainage orifice in fluid communication with the chamber to convey drops of liquid out of the chamber;

the nozzle includes at least one common internal fluid passage fluidly connected to a plurality of spatially displaced fluid channels each having a same channel shape and size to facilitate substantially equal flow out of each channel, each channel being defined by a fluid receiving end and a fluid exit end; and the nozzle includes a plurality of downwardly extending drop forming surfaces coupled to the fluid exit ends of each of the plurality of fluid channels.

32. A liquid dispensing device for controllably dispensing drops of liquid from a container comprising:

means for ejecting the liquid from the container, and nozzle means, interactive with the ejecting means, for directing ejected liquid into a drop forming chamber external to the container;

the drop forming chamber being formed by a plurality of interconnnected walls and adapted to receive the nozzle means wherein at least a first of the interconnected walls lies adjacent the nozzle means and includes a plurality of adjacent fluid wells for temporarily trapping ejected liquid as the liquid drains toward a primary reservoir with a drainage orifice in the chamber; and means coupled to the chamber for guiding draining liquid to a selected surface.

33. The liquid dispensing device of claim 32 further comprising:

a secondary reservoir that receives fluid from the primary reservoir through serial fluid communication, for facilitating evaporation of liquid and having a drainage orifice for receiving fluid overflow from the secondary reservoir; and a liquid flow guide connected to the drainage orifice for guiding liquid from the secondary reservoir.

34. The liquid dispensing device of claim 32 wherein the chamber is partitioned into a plurality of cavities, each cavity further comprising a separate primary reservoir with a separate drainage orifice, and each cavity coupled with a separate means for guiding draining drops.

35. The liquid dispensing device of claim 32 further comprising means in fluid contact with the primary reservoir, for absorbing a portion of the liquid to facilitate aromatic dispensing of a portion of the liquid in the primary reservoir.

36. The liquid dispensing device of claim 35 further comprising:
a housing having a convection passage defined therein for directing airflow over the means for absorbing liquid to facilitate aromatic dispensing of the liquid into the air.

37. The liquid dispensing device of claim 36 wherein the housing further comprises:
key means for cooperatively engaging the container.

38. The liquid dispensing device of claim 32 where the guiding means includes:
at least one secondary reservoir that receives liquid from the primary reservoir through serial fluid communication; and
at least one flow tube coupled with the at least one secondary reservoir to guide liquid therefrom.

39. A liquid dispensing device for controllably dispensing drops of liquid from a container comprising:
pump means, operative with the container containing the liquid, for ejecting the liquid from the container;
pump actuator means interactive with the pump means for activating the pump means;
timing means coupled to the actuator means for selectively activating the actuator means at predetermined intervals;
a chamber external to the container and having a plurality of cavities;
nozzle means, cooperative with the pump actuator means and the chamber, for simultaneously directing equal amounts of ejected liquid into the plurality of cavities, the nozzle means further including a plurality of fluid channels each having an integral drip tab extending downwardly from one end, the other ends of the fluid channels merging into a common cavity within the nozzle;
each of the cavities having an opening to receive one of the integral drip tabs, each cavity further including fluid wells for regulating liquid flow and for facilitating evaporation of the liquid, and a drainage orifice coupled to each cavity for separately guiding draining drops from each of the cavities.

40. A nozzle for dispensing drops of fluid comprising:
at least one common internal fluid passage fluidly connected to a plurality of spatially displaced fluid channels each having a same channel shape and size to facilitate substantially equal liquid flow out each channel, each channel being defined by a fluid receiving end and a fluid exit end, the fluid receiving end receiving fluid from a fluid source; the nozzle further including a plurality of downwardly extending drop forming tabs coupled to the fluid exit ends of each of the plurality of fluid channels.

41. The nozzle of claim 40 wherein each tab comprises a first downwardly extending surface for receiving the fluid to form drops of the fluid as the fluid flows over the first surface.

42. The nozzle of claim 41 wherein each first surface has a tip at the bottom end thereof, each tab further comprising a second surface opposite the first surface, each second surface extending away from the tip of the first surface at an angle less than ninety degrees with respect to the first surface to prevent the flow of fluid along the second surface.

43. The nozzle of claim 40 wherein each tab includes a first surface which tapers inwardly towards a tip of the tab to direct the flow of fluid drops to the tip of the tab as the fluid drops are formed on the first surface.

44. The nozzle device of claim 40 further comprising an exterior surface area for receiving a pump actuating mechanism.

45. A method for dispensing liquid in drop form from a container, the method comprising the steps of:
ejecting the liquid through a nozzle from the container at predetermined intervals using a timed actuator means;
forming drops of liquid by directing the ejected liquid over a drip tab extending from an exit orifice of the nozzle into a partially open external chamber; and
conveying the drops from the chamber through fluid path means in communication with the chamber.

46. The method of claim 45 wherein the step of ejecting includes ejecting substantially equal volumes of liquid out of a plurality of channels in the nozzle during each predetermined interval.

47. The method of claim 45 comprising the step of emitting vapor produced from the drops in the chamber to odorize an area in a room.

48. The method of claim 45 wherein the step of ejecting the liquid comprises the step of activating the actuator means at predetermined intervals to contact a pump means for pumping the liquid from the container.

49. A method for dispensing liquid in drop form from a container, the method comprising the steps of:
ejecting the liquid through a nozzle from the container at predetermined intervals using a timed actuator means;
directing the ejected liquid over a series of fluid wells in a chamber that receives the nozzle; and
guiding the drops from the chamber to a selected surface through a guide tube connected to the chamber.

50. The method of claim 49 wherein directing the ejected liquid includes passing fluid over at least one drip tab on the nozzle.

51. A liquid dispensing device for controllably dispensing drops of liquid from a container comprising:
a housing having at least two drainage areas each having a drainage orifice;
liquid ejection means for dispensing liquid;
flow guide tubes operatively connected to the drainage orifices, defining a plurality of flow paths; and
liquid absorbent diffuser means in the housing for absorbing liquid ejected from the liquid ejection means wherein the diffuser means includes at least two protruding fingers at a bottom thereof, each finger directing liquid into one of the drainage areas with equal amounts of liquid being directed by each finger to each drainage area and into each of the plurality of flow paths.

52. The liquid dispensing device of claim 51 wherein the liquid ejection means comprises:
an electronically actuated motor;
a cam moved by the motor; and
a nozzle depressed by the cam to eject liquid from the container.

53. A liquid dispensing device for controllably dispensing drops of liquid from a container comprising:
a motor actuated liquid ejection system operating upon an actuator associated with the container for selectively ejecting liquid from the container;
a nozzle in fluid communication with the container for receiving the ejected liquid and forming the ejected liquid into drops;

a chamber, external to the container, in which the liquid drops are formed by the nozzle;

the chamber having at least one drainage orifice in fluid communication with the chamber to convey drops of liquid out of the chamber.

54. A liquid dispensing device for controllably dispensing drops of liquid from a container comprising:

means for ejecting the liquid from the container;

means for receiving the ejected liquid and forming the ejected liquid into drops;

a chamber, external to the container, in which the liquid drops are formed by the receiving and drop-forming means;

the chamber including a plurality of primary reservoirs for accumulating drops of liquid dispensed from the receiving and drop-forming means;

each primary reservoir having a drainage orifice in fluid communication with the reservoir to convey drops of liquid out of the chamber;

at least one secondary reservoir that receives liquid through the drainage orifice of at least one of the primary reservoirs through serial fluid communication; and at least one flow tube coupled with the at least one secondary reservoir to guide liquid therefrom.

* * * * *

UNITED STATES PATENT AND TRADEMARK OFFICE
CERTIFICATE OF CORRECTION

PATENT NO. : 5,449,117
DATED : Sep. 12, 1995
INVENTOR(S) : Kenneth J. Muderlak; Rocky Shieh It is certified that error appears in the above-indentified patent and that said Letters Patent is hereby corrected as shown below:

In column 4, line 58, insert —4.— after "shown in FIG.".

In column 14, line 20, delete "the one/two switch", and insert therefor —the "one/two" switch—.

In column 17, line 8, delete "Upon", and insert therefor —upon—.

In column 18, line 54, after "drainage orifice" insert —in—.

In column 19, line 11, delete "dropsy;", and insert therefor —drops;—.

Signed and Sealed this

Twenty-third Day of January, 1996

Attest:

BRUCE LEHMAN

*Attesting Officer*     *Commissioner of Patents and Trademarks*